United States Patent
Wong et al.

(10) Patent No.: US 6,555,319 B2
(45) Date of Patent: *Apr. 29, 2003

(54) ANTIBODIES FOR INHIBITING BLOOD COAGULATION AND METHODS OF USE THEREOF

(75) Inventors: Hing C. Wong, Fort Lauderdale, FL (US); Jin-An Jiao, Fort Lauderdale, FL (US); Esperanza Liliana Nieves, Plantation, FL (US); Lawrence Luepschen, Miami, FL (US)

(73) Assignee: Sunol Molecular Corporation, Miramar, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/293,854

(22) Filed: Apr. 16, 1999

(65) Prior Publication Data

US 2002/0168357 A1 Nov. 14, 2002

Related U.S. Application Data

(63) Continuation of application No. 08/814,806, filed on Mar. 10, 1997, now Pat. No. 5,986,065.

(51) Int. Cl.[7] .................. G01N 33/53; C07K 16/00; C07K 16/18; C07K 16/28; C07K 16/36
(52) U.S. Cl. ................. 435/7.1; 530/387.1; 530/388.1; 530/388.15; 530/387.3
(58) Field of Search ................ 530/387.1, 388.1, 530/388.15, 387.3; 435/7.1

(56) References Cited

U.S. PATENT DOCUMENTS

| | | | |
|---|---|---|---|
| 5,216,132 A | 6/1993 | Basi | 530/387.3 |
| 5,223,427 A | 6/1993 | Edgington | 435/240.27 |
| 5,552,300 A | 9/1996 | Makrides et al. | 435/69.1 |
| 5,986,065 A | * 11/1999 | Wong | 530/388.22 |

FOREIGN PATENT DOCUMENTS

| | | |
|---|---|---|
| EP | 420937 B1 | 10/1991 |
| WO | WO 91/18019 | 11/1991 |
| WO | WO 96/13593 | 5/1996 |
| WO | WO 96/18105 | 6/1996 |

OTHER PUBLICATIONS

S. Ward, *Communications*, pp. 885–890 (1992).
C. Schlueter et al., *J. Mol. Biol.*, 256:859–869 (1996).
T. Onda et al., *Molecular Immunology*, 32(17–18):1387–1397 (1995).
J. Novotny et al., *Proc. Natl. Acad. Sci. USA*, 88:8646–8650 (1991).
C. Wulfing et al., *J. Mol. Biol.*, 242:655–669 (1994).
I. Kurucz et al., *Proc. Natl. Acad. Sci. USA*, 90:3830–3834 (1993).
S. Parmley et al., *Gene*, 73:305–318 (1988).
G. Smith et al., *Mehods in Enzymology*, 217:228–257 (1993).
C. Chothia et al., *The EMBO Journal*, 7(12):3745–3755 (1988).
W. Soo Hoo et al., *Proc. Natl. Acad. Sci. USA*, 89:4759–4763 (1992).
E. Ward, *Scand. J. Immunol.*, 34:215–220 (1991).
A. Lin et al., *Science*, 249:677–679 (1990).
C. Gregoire et al., *Proc. Natl. Acad. Sci. USA*, 88:8077–8081 (1991).
N. Gasciogne et al., *Proc. Natl. Acad. Sci. USA*, 84:2936–2940 (1987).
R. Mariuzza et al., *The Journal of Biological*, 264(13):7310–7316 (1989).
J. Kappler et al., *Proc. Natl. Acad. Sci. USA*, 91:8462–8466 (1994).
Rao et al., *Thrombosis Research*, 56:109–118 (1989).
Fiore et al., *Blood*, 80(12):3127–3134 (1992).
Clarke et al., *The Journal of Immunology*, 145:2286–96 (1990).
Ragni et al., *Circulation*, 93:1913–1918 (1996).
George et al., *Macromolecular Sequencing and Synthesis*, Alan Riss, pp. 127–149 (1988).
Groves et al., *Hybridoma*, 6(1):71–76 (1987).
*Illustrated Dictionary of Immunology*, Cruse et al., CRC Press (1995).
Morrison, *Ann. Rev. Immunol.*, 10:239–265 (1992).

* cited by examiner

Primary Examiner—Elizabeth Kemmerer
Assistant Examiner—Eliane Lazar-Wesley
(74) Attorney, Agent, or Firm—Peter F. Corless; Robert L. Buchanan; Edwards & Angell, LLP

(57) ABSTRACT

The invention includes antibodies that provide superior anti-coagulant activity by binding native human TF with high affinity and specificity. Antibodies of the invention can effectively inhibit blood coagulation in vivo. Antibodies of the invention can bind native human TF, either alone or present in a TF:VIIa complex, effectively preventing factor X binding to TF or that complex, and thereby reducing blood coagulation. Preferred antibodies of the invention specifically bind a conformational epitope predominant to native human TF, which epitope provides an unexpectedly strong antibody binding site.

40 Claims, 9 Drawing Sheets

H36.D2.B7 ANTI-TISSUE FACTOR LIGHT CHAIN VARIABLE REGION

GACATTCAGATGACCCAGTCTCCAGTCTCCTGCCTCTCCAGTCTCTGGGAGAAAGTGTCACCATCACATGC
 D  I  Q  M  T  Q  S  P  A  S  Q  S  A  S  L  G  E  S  V  T  I  T  C

CTGGCAAGTCAGAGTGATACATTGGTTAGCATGGTATCAGCAGAAACCAGGGAAATCTCCTCAGCTC
 L  A  S  Q  T  I  D  T    W  L  A  W  Y  Q  Q  K  P  G  K  S  P  Q  L

CTGATTTATGCTGCCACCAACTTGGCAGATGGGGTCCCATCAAGGTTCAGTGGCAGTGGATCTGGCACA
 L  I  Y  A  A  T  N  L  A  D    G  V  P  S  R  F  S  G  S  G  S  G  T

AAATTTCTTCAAGATCAGCAGCCTACAGGCTGAAGATTTTGTAAATTATTACTGTGTCAACAAGTTTAC
 K  F  S  F  K  I  S  S  L  Q  A  E  D  F  V  N  Y  Y  C    Q  Q  V  Y

AGTTCTCCATTCACGTTCGGTGCTGGGACCAAGCTGGAGCTGAAA
 S  S  P  F  T    F  G  A  G  T  K  L  E  L  K

FIG. 1A

H36.D2.B7 ANTI-TISSUE FACTOR HEAVY CHAIN VARIABLE REGION

GAGATCCAGCTGCAGCAGTCTGGGACCTGAGCTGGTGAAGCCTGGGGCTTCAGTGCAGGTATCCTGCAAG
 E  I  Q  L  Q  Q  S  G  P  E  L  V  K  P  G  A  S  V  Q  V  S  C  K

ACTTCTGGTTACTCATTCACT GACTACAACGTGTAC TGGGTGAGGCAGAGCCATGGAAAGAGCCTTGAG
 T  S  G  Y  S  F  <u>T  D  Y  N  V  Y</u>  W  V  R  Q  S  H  G  K  S  L  E

TGGATTGGA TATATTGATCCTTACTACAATGGTATTACTATCTACGACCAGAACTTCAAGGGCAAGGCCACA
 W  I  G  <u>Y  I  D  P  Y  Y  N  G  I  T  I  Y  D  Q  N  F  K  G</u>  K  A  T

TTGACTGTTGACAAGTCTTCCACCACAGCCTTCATGCATCTCAACAGCCTGACTTCTGACGACTCTGCA
 L  T  V  D  K  S  S  T  T  A  F  M  H  L  N  S  L  T  S  D  D  S  A

GTTTATTTCTGTGCAAGAGATGTGACTACGGCCCTTGACTTCTGGGGCCAAGGCACCACTCTCACAGTC
 V  Y  F  C  A  R  <u>D  V  T  T  A  L  D  F</u>  W  G  Q  G  T  T  L  T  V

TCCTCA
 S  S

FIG. 1B

| ANTIBODY | APPARENT $K_1$, M$^{-1}$ | APPARENT $K_1$, M |
|---|---|---|
| BY ELISA | | |
| D2 | $5.2 \times 10^9$ | $1.9 \times 10^{-10}$ |
| I47 | $6.5 \times 10^9$ | $1.5 \times 10^{-10}$ |
| K73 | $9.8 \times 10^9$ | $1.0 \times 10^{-10}$ |
| K80 | $2.3 \times 10^9$ | $4.3 \times 10^{-10}$ |
| L102 | $2.5 \times 10^9$ | $4.0 \times 10^{-10}$ |
| L133 | $1.7 \times 10^9$ | $5.9 \times 10^{-10}$ |
| BY BIACore | | |
| H36 | $3.1 \times 10^{10}$ | $3.2 \times 10^{-11}$ |
| I43 | $2.3 \times 10^9$ | $4.3 \times 10^{-10}$ |
| I47 | $3.2 \times 10^9$ | $3.1 \times 10^{-10}$ |
| L133 | $4.6 \times 10^9$ | $2.2 \times 10^{-10}$ |
| M107 | $1.1 \times 10^9$ | $9.1 \times 10^{-10}$ |

FIG. 2

| ANTIBODY NAME | % INHIBITION ANTIBODY PREINCUBATED WITH TF/VIIa |
|---|---|
| D1 | 0 |
| D1B | 1 |
| H31 | 4 |
| H36 | 95 |
| I43 | 1 |
| J131 | 7 |
| K80 | 0 |
| K82 | 0 |
| K87 | 1 |
| L97B | 7 |
| L101 | 0 |
| L102 | 0 |
| L105 | 0 |
| L133 | 0 |
| M5 | 1 |
| M107 | 34 |

FIG. 3

| ANTIBODY NAME | % INHIBITION TF PREINCUBATED WITH ANTIBODY PRIOR TO ADDITION OF VIIa | % INHIBITION TF PREINCUBATED WITH VIIa PRIOR TO ADDITION OF ANTIBODY |
|---|---|---|
| D1 | 15 | nd |
| D1B | 48 | 12.7 |
| H31 | 64 | 21 |
| H36 | 0 | 0 |
| I43 | 68 | 55 |
| J131 | 38 | 11 |
| K80 | 12 | nd |
| K82 | 0 | nd |
| K87 | 0 | nd |
| L96 | 0 | nd |
| L101 | 38 | 11 |
| L102 | 14 | nd |
| L105 | 4 | nd |
| L133 | 13 | nd |
| M5 | 0 | nd |
| M107 | 0 | nd |

FIG. 4

| [rhTF], nM | [H36.D2], nM | H36.D2/rhTF MOLAR RATIO | CLOTTING TIME (SECONDS) | % INHIBITION OF rhTF FUNCTION |
|---|---|---|---|---|
| 0.0048 | 0<br>1.61<br>3.23 | 0<br>335.4<br>670.8 | 102.3<br>114.3<br>121.3 | 0<br>31.3<br>45.8 |
| 0.023 | 0<br>1.61<br>3.23<br>6.45 | 0<br>70.0<br>140.0<br>280.4 | 77.6<br>85.3<br>91.1<br>99.6 | 0<br>52.2<br>65.2<br>73.9 |
| 0.092 | 0<br>3.23<br>6.45<br>12.90 | 0<br>35.1<br>70.1<br>140.2 | 49.3<br>65.8<br>88.5<br>113.3 | 0<br>65.2<br>90.2<br>95.7 |
| 0.46 | 0<br>6.45<br>12.90<br>32.30 | 0<br>14.0<br>28.0<br>70.2 | 32.6<br>52.7<br>80.2<br>117.9 | 0<br>82.4<br>96.7<br>99.3 |
| 2.30 | 0<br>16.10<br>32.30<br>64.50 | 0<br>7.0<br>14.0<br>28.0 | 23.9<br>47.1<br>95.2<br>115.3 | 0<br>94.4<br>99.7<br>99.9 |
| 11.52 | 0<br>16.10<br>32.30<br>64.50<br>161.30 | 0<br>1.4<br>2.8<br>5.6<br>14.0 | 22.2<br>30.2<br>46.0<br>87.6<br>114.0 | 0<br>93.4<br>98.8<br>99.9<br>100.0 |

FIG. 5

| H36.D2 CONCENTRATION (ng) | % INHIBITION CELLS (TF/FVII) AND H36.D2 PREINCUBATED PRIOR TO FX ADDITION | % INHIBITION FX AND H36.D2 ARE ADDED SIMULTANEOUSLY TO CELLS (TF/FVII) |
|---|---|---|
| 0 | 0 | 0 |
| 50 | 88 | nd |
| 100 | 92 | nd |
| 200 | 97 | nd |
| 800 | nd | 76 |
| 1600 | nd | 78 |
| 3200 | nd | 92 |

FIG. 7

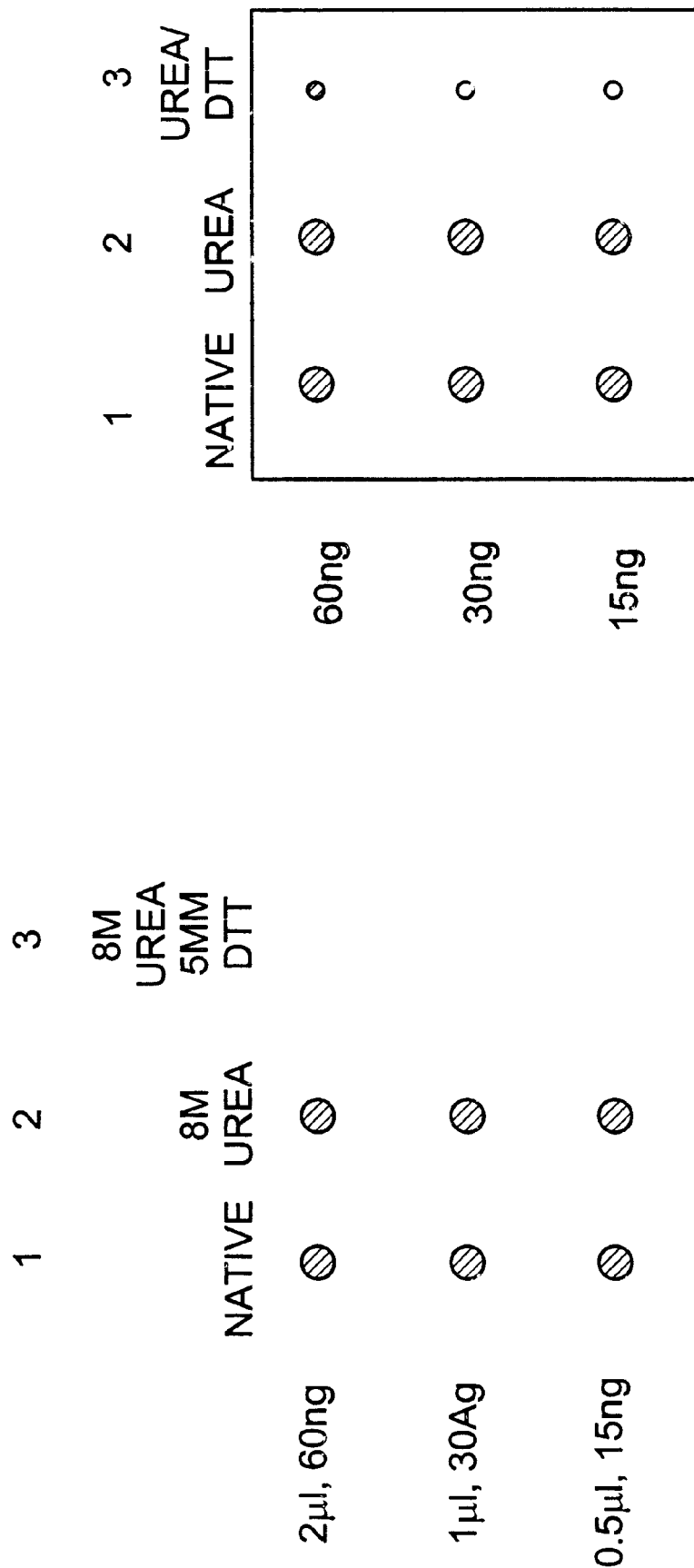

ANTIBODIES FOR INHIBITING BLOOD COAGULATION AND METHODS OF USE THEREOF

This application is a continuation of application Ser. No. 08/814,806 filed on Mar. 10, 1997, now U.S. Pat. No. 5,986,065 and which designated the U.S.

BACKGROUND OF THE INVENTION

1. Field of the Invention

The present invention relates to novel antibodies and methods of using the antibodies to inhibit blood coagulation. In particular, the invention relates to novel antibodies that can specifically bind native human tissue factor with high affinity. The antibodies of the invention are useful for a variety of applications, particularly for reducing blood coagulation in vivo.

2. Background

Blood clotting assists homeostasis by minimizing blood loss. Generally, blood clotting requires vessel damage, platelet aggregation, coagulation factors and inhibition of fibrinolysis. The coagulation factors act through a cascade that relates the vessel damage to formation of a blood clot (see generally L. Stryer, Biochemistry, 3rd Ed, W. H. Freeman Co., New York; and A. G. Gilman et al., The Pharmacological Basis of Therapeutics, 8th Edition, McGraw Hill Inc., New York, pp. 1311–1331).

There is general agreement that factor X (FX) activation to factor Xa (FXa) is a critical step in the blood coagulation process. Generally, FX is converted to FXa by binding a catalytically active complex that includes "tissue factor" (TF). TF is a controllably-expressed cell membrane protein that binds factor VII/VIIa to produce the catalytically active complex (TF:VIIa). A blood clot follows FXa-mediated activation of prothrombin. Blood clotting can be minimized by inactivation of TF to non-native forms which cannot optimally produce the TF:VIIa complex. Excessive formation of FXa is believed to contribute to various thromboses including restenosis.

Thrombosis may be associated with invasive medical procedures such as cardiac surgery (e.g. angioplasty), abdominothoracic surgery, arterial surgery, deployment of an implementation (e.g., a stent or catheter), or endarterectomy. Further, thrombosis may accompany various thromboembolic disorders and coagulopathies such as a pulmonary embolism (e.g., atrial fibrillation with embolization) and disseminated intravascular coagulation, respectively. Manipulation of body fluids can also result in an undesirable thrombus, particularly in blood transfusions or fluid sampling, as well as procedures involving extracorporeal circulation (e.g., cardiopulmonary bypass surgery) and dialysis.

Anti-coagulants are frequently used to alleviate or avoid blood clots associated with thrombosis. Blood clotting often can be minimized or eliminated by administering a suitable anti-coagulant or mixture thereof, including one or more of a coumarin derivative (e.g., warfin and dicumarol) or a charged polymer (e.g., heparin, hirudin or hirulog). See e.g., Gilman et al., supra, R. J. Beigering et al., Ann. Hemathol., 72:177 (1996); J. D. Willerson, Circulation, 94:866 (1996).

However, use of anti-coagulants is often associated with side effects such as hemorrhaging, re-occlusion, "white-clot" syndrome, irritation, birth defects, thrombocytopenia and hepatic dysfunction. Long-term administration of anti-coagulants can particularly increase risk of life-threatening illness (see e.g., Gilman et al., supra).

Certain antibodies with anti-platelet activity have also been used to alleviate various thromboses. For example, ReoPro™ is a therapeutic antibody that is routinely administered to alleviate various thromboembolic disorders such as those arising from angioplasty, myocardial infarction, unstable angina and coronary artery stenoses. Additionally, ReoPro™ can be used as a prophylactic to reduce the risk of myocardial infarction and angina (J. T. Willerson, Circulation, 94:866 (1996); M. L. Simmons et al., Circulation, 89:596 (1994)).

Certain anti-coagulant antibodies are also known. Particularly, certain TF-binding antibodies have been reported to inhibit blood coagulation, presumably by interfering with assembly of a catalytically active TF:VIIa complex (see e.g., Jeske et al., SEM in THROM. and HEMO, 22:213 (1996); Ragni et al., Circulation, 93:1913 (1996); European Patent No. 0 420 937 B1; W. Ruf et al., Thromb. Haemosp., 66:529 (1991); M. M. Fiorie et al., Blood, 8:3127 (1992)).

However, current TF-binding antibodies exhibit significant disadvantages which can minimize their suitably as anti-coagulants. For example, current TF-binding antibodies do not exhibit sufficient binding affinity for optimal anti-coagulant activity. Accordingly, for many thrombotic conditions, to compensate for such ineffective binding affinities, unacceptably high antibody levels must be administered to minimize blood coagulation. Further, current TF-binding antibodies do not effectively discriminate between native TF and non-native forms of TF, i.e. the current antibodies do not exhibit sufficient binding specificity. Still further, current TF-binding antibodies can not prevent FX from binding to TF and/or TF:VIIa complex.

It would thus be desirable to have an anti-coagulant antibody that binds native human TF with high affinity and selectivity to thereby inhibit undesired blood coagulation and the formation of blood clots. It would be further desirable to have such an anti-coagulant antibody that prevents the binding of Factor X to TF/VIIa complex.

SUMMARY OF THE INVENTION

We have now discovered antibodies that provide superior anti-coagulant activity by binding native human TF with high affinity and specificity. Antibodies of the invention can effectively inhibit blood coagulation in vivo. Antibodies of the invention can bind native human TF, either alone or present in a TF:VIIa complex, effectively preventing factor X binding to TF or that complex, and thereby reducing blood coagulation.

Preferred antibodies of the invention are monoclonal and specifically bind a conformational epitope predominant to native human TF, which epitope provides an unexpectedly strong antibody binding site. Indeed, preferred antibodies of the invention bind to native human TF at least about 5 times greater, more typically at least about ten times greater than the binding affinity exhibited by prior anti-coagulant antibodies. Additionally, preferred antibodies of the invention are selective for native human TF, and do not substantially bind non-native or denatured TF. H36.D2.B7 (secreted by hybridoma ATCC HB-12255) is an especially preferred antibody of the invention.

Preferred antibodies of the invention bind TF so that FX does not effectively bind to the TF/factor VIIa complex whereby FX is not effectively converted to its activated form (FXa). Preferred antibodies of the invention can inhibit TF function by effectively blocking FX binding or access to TF molecules. See, for instance, the results of Example 3 which follows.

Preferred antibodies of the invention also do not significantly inhibit the interaction or binding between TF and factor VIIa, or inhibit activity of a TF:factor VIIa complex with respect to materials other than FX. See, for instance, the results of Example 4 which follows.

The invention also provides nucleic acids that encode antibodies of the invention. Nucleic acid and amino acid sequences (SEQ ID:NOS 1–4) of variable regions of H36.D2.B7 are set forth in FIGS. 1A and 1B of the drawings.

In preferred aspects, the invention provides methods for inhibiting blood coagulation and blood clot formation, and methods for reducing human TF levels.

In general, antibodies of the invention will be useful to modulate virtually any biological response mediated by FX binding to TF or the TF:VIIa complex, including blood coagulation as discussed above, inflammation and other disorders.

Antibodies of the invention are particularly useful to alleviate various thromboses, particularly to prevent or inhibit restenosis, or other thromboses following an invasive medical procedure such as arterial or cardiac surgery (e.g., angioplasty). Antibodies of the invention also can be employed to reduce or even effectively eliminate blood coagulation arising from use of medical implementation (e.g., a catheter, stent or other medical device). Preferred antibodies of the invention will be compatible with many anti-coagulant, anti-platelet and thrombolytic compositions, thereby allowing administration in a cocktail format to boost or prolong inhibition of blood coagulation.

Antibodies of the invention also can be employed as an anti-coagulant in extracorporeal circulation of a mammal, particularly a human subject. In such methods, one or more antibodies of the invention is administered to the mammal in an amount sufficient to inhibit blood coagulation prior to or during extracorporeal circulation such as may be occur with cardiopulmonary bypass surgery, organ transplant surgery or other prolonged surgeries.

Antibodies of the invention also can be used as a carrier for drugs, particularly pharmaceuticals targeted for interaction with a blood clot such as strepokinase, tissue plasminogen activator (t-PA) or urokinase. Similarly, antibodies of the invention can be used as a cytotoxic agent by conjugating a suitable toxin to the antibody. Conjugates of antibodies of the invention also can be used to reduce tissue factor levels in a mammal, particularly a human, by administering to the mammal an effective amount of an antibody of the invention which is covalently linked a cell toxin or an effector molecule to provide complement-fixing ability and antibody-dependent cell-mediated cytotoxicity, whereby the antibody conjugate contacts cells expressing tissue factor to thereby reduce tissue factor levels in the mammal.

Antibodies of the invention also can be employed in in vivo diagnostic methods including in vivo diagnostic imaging of native human TF.

Antibodies of the invention also can be used in in vitro assays to detect native TF in a biological sample including a body fluid (e.g., plasma or serum) or tissue (e.g., a biopsy sample). More particularly, various heterogeneous and homogeneous immunoassays can be employed in a competitive or non-competitive format to detect the presence and preferably an amount of native TF in the biological sample.

Such assays of the invention are highly useful to determine the presence or likelihood of a patient having a blood coagulation or a blood clot. That is, blood coagulation is usually accompanied by TF expression on cells surfaces such as cells lining the vasculature. In the absence of blood coagulation, TF is not usually expressed. Thus, the detection of TF in a body fluid sample by an assay of the invention will be indicative of blood coagulation.

Antibodies of the invention also can be used to prepare substantially pure native TF, particularly native human TF, from a biological sample. Antibodies of the invention also can be used for detecting and purifying cells which express native TF.

Antibodies of the invention also can be employed as a component of a diagnostic kit, e.g. for detecting and preferably quantitating native TF in a biological sample. Other aspects of the invention are discussed infra.

BRIEF DESCRIPTION OF THE DRAWINGS

FIGS. 1A and 1B shows the nucleic acid (SEQ ID NOS:1 and 3) and amino acid (SEQ ID NOS:2 and 4) sequences of light chain and heavy chain variable regions of H36.D2.B7 with hypervariable regions (CDRs or Complementarity Determining Regions) underlined (single underline for nucleic acid sequences and double underline for amino acid sequences).

FIG. 2 shows association ($K_a$) and disassociation ($K_d$) constants of anti-tissue factor antibodies as determined by ELISA or BIACore analysis.

FIG. 3 shows inhibition of TF:VIIa complex mediated FX activation by pre-incubation with anti-tissue factor antibodies.

FIG. 4 shows inhibition of TF/VIIa activity toward the FVIIa-specific substrate S-2288 by anti-tissue factor antibodies.

FIG. 5 shows the capacity of the H36 antibody to increase prothrombin time (PT) in a TF-initiated coagulation assay.

FIG. 6A: H36.D2 was pre-incubated with the FT:VIIa complex prior to adding FX. FIG. 6B: H36.D2, TF:VIIa and FX were added simultaneously.

FIG. 7 shows inhibition of TF:VIIa activity by the H36.D2 antibody in a J-82 cell activation assay.

FIGS. 8A and 8B are representations of dot blots showing that the H36.D2 antibody binds a conformational epitope on rhTF. Lane 1-native rHTF, Lane 2-native rhTF treated with 8M urea, Lane 3-native rHTF treated with 8M urea and 5 mM DTT. In FIG. 8A, the blot was exposed for approximately 40 seconds, whereas in FIG. 8B, the blot was exposed for 120 seconds.

DETAILED DESCRIPTION OF THE INVENTION

Figure 6A:
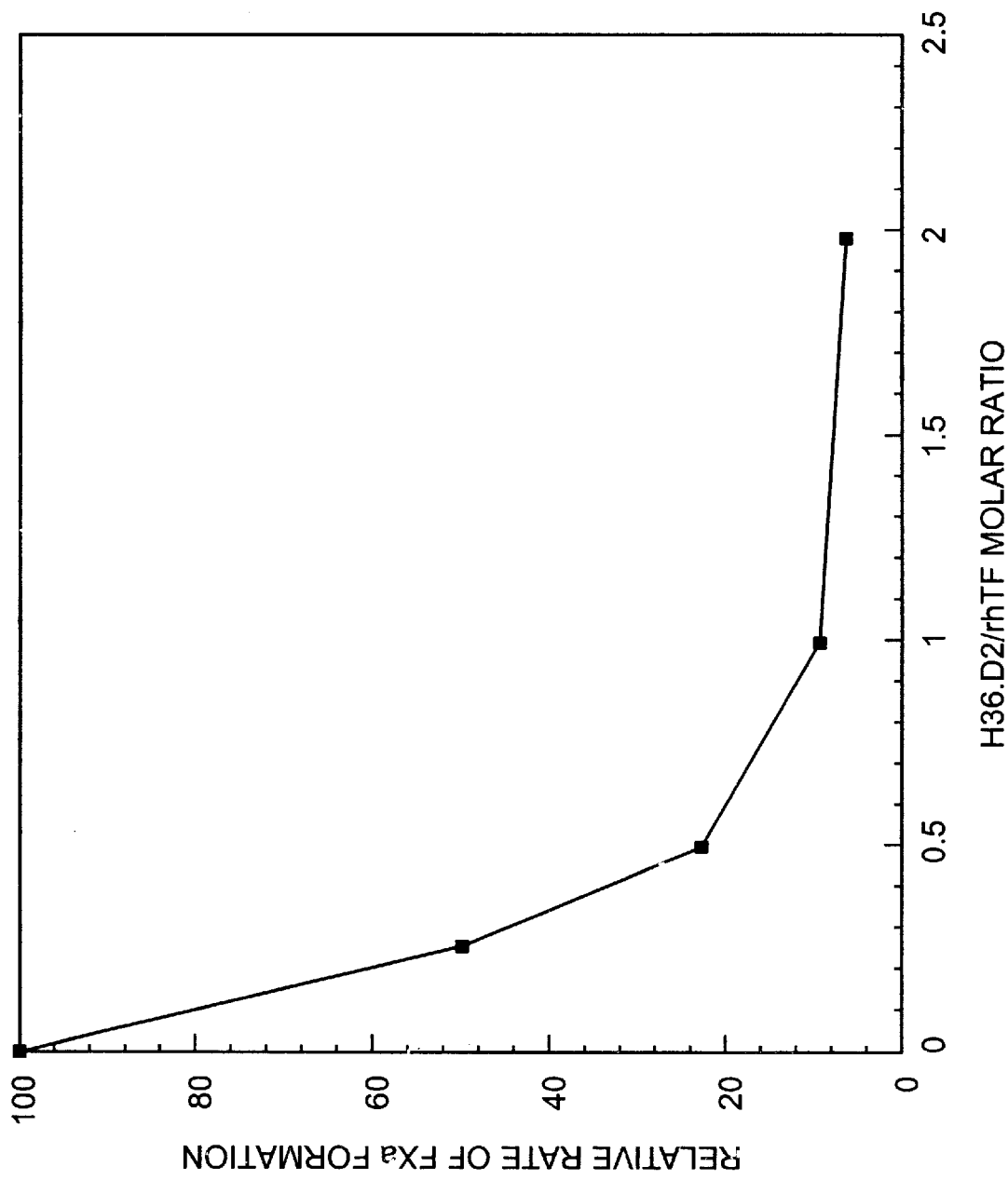
FIGS. 6A and 6B graphically show the relationship between FXa formation and molar ratio of the H36.D2 antibody and rHTF.

As discussed above, preferred antibodies of the invention exhibit substantial affinity for native human TF. In particular, preferred antibodies of the invention exhibit an association constant ($K_a$, $M^{-1}$) for native human TF of at least about $1 \times 10^8$ as determined by surface plasmon analysis (particularly, BIACore analysis in accordance with the procedures of Example 1 which follows), more preferably at least about $5 \times 10^8$ as determined by surface plasmon analysis, still more preferably a $K_a$ ($K_a$, $M^{-1}$) for native human TF of at least about $1 \times 10^{10}$ as determined by surface plasmon analysis. Such substantial binding affinity of antibodies of the invention contrast sharply from much lower binding affinities of previously reported antibodies.

In this regard, a quite low of effective concentration of an antibody of the invention can be employed, e.g. a relatively low concentration of antibody can be employed to inhibit TF function as desired (e.g. at least about 95, 98 or 99 percent inhibition) in an in vitro assay such as described in Example 3 which follows.

The preferred antibodies are also highly specific for native human TF, and preferably do not substantially bind with non-native TF. Preferred antibodies do not substantially bind non-native TF or other immunologically unrelated molecules as determined, e.g. by standard dot blot assay (e.g. no or essentially no binding to non-native TF visually detected by such dot blot assay). References herein to "non-native TF" mean a naturally-occurring or recombinant human TF that has been treated with a choatropic agent so that the TF is denatured. Typical choatropic agents include a detergent (e.g. SDS), urea combined with dithiothreotol or β-mercaptoethanol; guanidine hydrochloride and the like. The H36, H36.D2 or H36.D2.B7 antibody does not substantially bind to such non-native TF. See, for instance, the results of Example 8 which follows and is a dot blot assay.

As discussed above, preferred antibodies of the invention also bind with TF so that FX does not effectively bind to the TF/factor VIIa complex whereby FX is not effectively converted to its activated form (FXa). Particularly preferred antibodies of the invention exhibit will strongly inhibit FX activity to a TF/factor VIIa complex, e.g. an inhibition of at least about 50%, more preferably at least about 80%, and even more preferably at least about 90% or 95%, even at low TF concentrations such as less than about 1.0 nM TF, or even less than about 0.20 nM or 0.10 nM TF, as determined by a standard in vitro binding assay such as that of Example 3 which follows and includes contacting FX with a TF:factor VIIa complex both in the presence (i.e. experimental sample) and absence (i.e. control sample) of an antibody of the invention and determining the percent difference of conversion of FX to FXa between the experimental and control samples.

Antibodies of the invention are preferably substantially pure when used in the disclosed methods and assays. References to an antibody being "substantially pure" mean an antibody or protein which has been separated from components which naturally accompany it. For example, by using standard immunoaffinity or protein A affinity purification techniques, an antibody of the invention can be purified from a hybridoma culture by using native TF as an antigen or protein A resin. Similarly, native TF can be obtained in substantially pure form by using an antibody of the invention with standard immunoaffinity purification techniques. Particularly, an antibody or protein is substantially pure when at least 50% of the total protein (weight % of total protein in a given sample) is an antibody or protein of the invention. Preferably the antibody or protein is at least 60 weight % of the total protein, more preferably at least 75 weight %, even more preferably at least 90 weight %, and most preferably at least 98 weight % of the total material. Purity can be readily assayed by known methods such as SDS (PAGE) gel electrophoresis, column chromatography (e.g., affinity chromatography) or HPLC analysis.

The nucleic acid (SEQ ID NOS: 1 and 3) and amino acid (SEQ ID NOS: 2 and 4) sequences of a preferred antibody of the invention (H36.D2.B7) are shown in FIGS. 1A and 1B of the drawings. SEQ ID NOS. 1 and 2 are the nucleic acid and amino acid respectively of the light chain variable region, and SEQ ID NOS. 3 and 4 are the nucleic acid and amino acid respectively of the heavy chain variable region, with hypervariable regions (CDRs or Complementarity Determining Regions) underlined in all of those sequences.

Additional preferred antibodies of the invention will have substantial sequence identity to either one or both of the light chain or heavy sequences shown in FIGS. 1A and 1B. More particularly, preferred antibodies include those that have at least about 70 percent homology (sequence identity) to SEQ ID NOS. 2 and/or 4, more preferably about 80 percent or more homology to SEQ ID NOS. 2 and/or 4, still more preferably about 85, 90 or 95 percent or more homology to SEQ ID NOS. 2 and/or 4.

Preferred antibodies of the invention will have high sequence identity to hypervariable regions (shown with double underlining in FIGS. 1A and 1B) of SEQ ID NOS. 2 and 4). Especially preferred antibodies of the invention will have one, two or three hypervariable regions of a light chain variable region that have high sequence identity (at least 90% or 95% sequence identity) to or be the same as one, two or three of the corresponding hypervariable regions of the light chain variable region of H36.D2.B7 (those hypervariable regions shown with underlining in FIG. 1A and are the following: 1) LASQTID (SEQ ID NO:5); 2) AATNLAD (SEQ ID NO:6); and 3) QQVYSSPFT (SEQ ID NO:7)).

Especially preferred antibodies of the invention also will have one, two or three hypervariable regions of a heavy chain variable region that have high sequence identity (at least 90% or 95% sequence identity) to or be the same as one, two or three of the corresponding hypervariable regions of the heavy chain variable region of H36.D2.B7 (those hypervariable regions shown with underlining in FIG. 1B and are the following: 1) TDYNVY (SEQ ID NO:8); 2) YIDPYNGITIYDQNFKG (SEQ ID NO:9); and 3) DVT-TALDF (SEQ ID NO:10).

Nucleic acids of the invention preferably are of a length sufficient (preferably at least about 100, 200 or 250 base pairs) to bind to the sequence of SEQ ID NO:1 and/or SEQ ID NO:3 under the following moderately stringent conditions (referred to herein as "normal stringency" conditions): use of a hybridization buffer comprising 20% formamide in 0.8M saline/0.08M sodium citrate (SSC) buffer at a temperature of 37° C. and remaining bound when subject to washing once with that SSC buffer at 37° C.

More preferably, nucleic acids of the invention (preferably at least about 100, 200 or 250 base pairs) will bind to the sequence of SEQ ID NO:1 and/or SEQ ID NO:3 under the following highly stringent conditions (referred to herein as "high stringency" conditions): use of a hybridization buffer comprising 20% formamide in 0.9M saline/0.09M sodium citrate (SSC) buffer at a temperature of 42° C. and remaining bound when subject to washing twice with that SSC buffer at 42° C.

Nucleic acids of the invention preferably comprise at least 20 base pairs, more preferably at least about 50 base pairs, and still more preferably a nucleic acid of the invention comprises at least about 100, 200, 250 or 300 base pairs.

Generally preferred nucleic acids of the invention will express an antibody of the invention that exhibits the preferred binding affinities and other properties as disclosed herein.

Preferred nucleic acids of the invention also will have substantial sequence identity to either one or both of the light chain or heavy sequences shown in FIGS. 1A and 1B. More particularly, preferred nucleic acids will comprise a sequence that has at least about 70 percent homology (sequence identity) to SEQ ID NOS. 1 and/or 3, more preferably about 80 percent or more homology to SEQ ID NOS. 1 and/or 3, still more preferably about 85, 90 or 95 percent or more homology to SEQ ID NOS. 1 and/or 3.

Particularly preferred nucleic acid sequences of the invention will have high sequence identity to hypervariable regions (shown with underlining in FIGS. 1A and 1B) of SEQ ID NOS. 1 and 3). Especially preferred nucleic acids include those that code for an antibody light chain variable region and have one, two or three sequences that code for hypervariable regions and have high sequence identity (at least 90% or 95% sequence identity) to or be the same as one, two or three of the sequences coding for corresponding hypervariable regions of H36.D2.B7 (those hypervariable regions shown with underlining in FIG. 1A and are the following: 1) CTGGCAAGTCAGACCATTGAT (SEQ ID NO:11); 2) GCTGCCACC AACTTGGCAGAT (SEQ ID NO:12); and 3) CAACAAGTTTACAGTTCT CCATTCACGT (SEQ ID NO:13)).

Especially preferred nucleic acids also code for an antibody heavy chain variable region and have one, two or three sequences that code for hypervariable regions and have high sequence identity (at least 90% or 95% sequence identity) to or be the same as one, two or three of the sequences coding for corresponding hypervariable regions of H36.D2.B7 (those hypervariable regions shown with underlining in FIG. 1B and are the following: 1) ACTGACTACAACGTGTAC (SEQ ID NO: 14); 2) TATATTGAT CCTTACAATGGTAT-TACTATCTACGACCAGAACTTCAAGGGC (SEQ ID NO:15); and 3) GATGTGACTACGGCCCTTGACTTC (SEQ ID NO:16)).

Nucleic acids of the invention are isolated, usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

Antibodies of the invention can be prepared by techniques generally known in the art, and are typically generated to a purified sample of native TF, typically native human TF, preferably purified recombinant human tissue factor (rhTF). Truncated recombinant human tissue factor or "rhTF" (composed of 243 amino acids and lacking the cytoplasmic domain) is particularly preferred to generate antibodies of the invention. The antibodies also can be generated from an immunogenic peptide that comprises one or more epitopes of native TF that are not exhibited by non-native TF. References herein to "native TF" include such TF samples, including such rhTF. As discussed above, monoclonal antibodies are generally preferred, although polyclonal antibodies also can be employed.

More particularly, antibodies can be prepared by immunizing a mammal with a purified sample of native human TF, or an immunogenic peptide as discussed above, alone or complexed with a carrier. Suitable mammals include typical laboratory animals such as sheep, goats, rabbits, guinea pigs, rats and mice. Rats and mice, especially mice, are preferred for obtaining monoclonal antibodies. The antigen can be administered to the mammal by any of a number of suitable routes such as subcutaneous, intraperitoneal, intravenous, intramuscular or intracutaneous injection. The optimal immunizing interval, immunizing dose, etc. can vary within relatively wide ranges and can be determined empirically based on this disclosure. Typical procedures involve injection of the antigen several times over a number of months. Antibodies are collected from serum of the immunized animal by standard techniques and screened to find antibodies specific for native human TF. Monoclonal antibodies can be produced in cells which produce antibodies and those cells used to generate monoclonal antibodies by using standard fusion techniques for forming hybridoma cells. See G. Kohler, et al., *Nature,* 256:456 (1975). Typically this involves fusing an antibody producing cell with an immortal cell line such as a myeloma cell to produce the hybrid cell. Alternatively, monoclonal antibodies can be produced from cells by the method of Huse, et al., *Science,* 256:1275 (1989).

One suitable protocol provides for intraperitoneal immunization of a mouse with a composition comprising purified rhTF complex conducted over a period of about two to seven months. Spleen cells then can be removed from the immunized mouse. Sera from the immunized mouse is assayed for titers of antibodies specific for rhTF prior to excision of spleen cells. The excised mouse spleen cells are then fused to an appropriate homogenic or heterogenic (preferably homogenic) lymphoid cell line having a marker such as hypoxanthine-guanine phosphoribosyltransferase deficiency (HGPRT$^-$) or thymidine kinase deficiency (TK$^-$). Preferably a myeloma cell is employed as the lymphoid cell line. Myeloma cells and spleen cells are mixed together, e.g. at a ratio of about 1 to 4 myeloma cells to spleen cells. The cells can be fused by the polyethylene glycol (PEG) method. See G. Kohler, et al., *Nature,* supra. The thus cloned hybridoma is grown in a culture medium, e.g. RPMI-1640. See G. E. More, et al., *Journal of American Medical Association,* 199:549 (1967). Hybridomas, grown after the fusion procedure, are screened such as by radioimmunoassay or enzyme immunoassay for secretion of antibodies that bind specifically to the purified rhTF, e.g. antibodies are selected that bind to the purified rhTF, but not to non-native TF. Preferably an ELISA is employed for the screen. Hybridomas that show positive results upon such screening can be expanded and cloned by limiting dilution method. Further screens are preferably performed to select antibodies that can bind to rhTF in solution as well as in a human fluid sample. The isolated antibodies can be further purified by any suitable immunological technique including affinity chromatography. A hybridoma culture producing the particular preferred H36.D2.B7 antibody has been deposited pursuant to the Budapest Treaty with the American Type Culture Collection (ATCC) at 10801 University Blvd., Mansassas, Va., 20110-2209. The hybridoma culture was deposited with the ATCC on Jan. 8, 1997 and was assigned Accession Number ATCC HB-12255.

For human therapeutic applications, it may be desirable to produce chimeric antibody derivatives, e.g. antibody molecules that combine a non-human animal variable region and a human constant region, to thereby render the antibodies less immunogenic in a human subject than the corresponding non-chimeric antibody. A variety of types of such chimeric antibodies can be prepared, including e.g. by producing human variable region chimeras, in which parts of the variable regions, especially conserved regions of the antigen-binding domain, are of human origin and only the hypervariable regions are of non-human origin. See also discussions of humanized chimeric antibodies and methods of producing same in S. L. Morrison, *Science,* 229:1202–1207 (1985); Oi et al., *BioTechniques,* 4:214 (1986); Teng et al., *Proc. Natl. Acad. Sci. U.S.A.,* 80:7308–7312 (1983); Kozbor et al., *Immunology Today,* 4:7279 (9183); Olsson et al., *Meth. Enzymol.,* 9:3–16 (1982). Additionally, transgenic mice can be employed. For example, transgenic mice carrying human antibody repertoires have been created which can be immunized with native human TF. Splenocytes from such immunized transgenic mice can then be used to create hybridomas that secrete human monoclonal antibodies that specifically react with native human TF as described above. See N. Lonberg et al., Nature, 368:856–859 (1994); L. L. Green et al., Nature Genet., 7:13–21 (1994); S. L. Morrison, *Proc. Natl. Acad. Sci. U.S.A.,* 81:6851–6855 (1994).

Nucleic acids of antibodies of the invention also can be prepared by polymerase chain reaction (see primers disclosed in Example 1 which follows). See generally, Sambrook et al., Molecular Cloning (2d ed. 1989). Such nucleic acids also can be synthesized by known methods, e.g. the phosphate triester method (see Oligonucleotide Synthesis, IRL Press (M. J. Gait, ed., 1984)), or by using a commercially available automated oligonucleotide synthesizer. Such a prepared nucleic acid of the invention can be employed to express an antibody of the invention by known techniques. For example, a nucleic acid coding for an antibody of the invention can be incorporated into a suitable vector by known methods such as by use of restriction enzymes to make cuts in the vector for insertion of the construct followed by ligation. The vector containing the inserted nucleic acid sequence, suitably operably linked to a promoter sequence, is then introduced into host cells for expression. See, generally, Sambrook et al., supra. Selection of suitable vectors can be made empirically based on factors relating to the cloning protocol. For example, the vector should be compatible with, and have the proper replicon for the host cell that is employed. Further, the vector must be able to accommodate the inserted nucleic acid sequence. Suitable host cells will include a wide variety of eukaryotic or prokaryotic cells such as *E. coli* and the like.

The molecular weight of the antibodies of the invention will vary depending on several factors such as the intended use and whether the antibody includes a conjugated or recombinantly fused toxin, pharmaceutical, or detectable label or the like. In general, an antibody of the invention will have a molecular weight of between approximately 20 to 150 kDa. Such molecular weights can be readily are determined by molecular sizing methods such as SDS-PAGE gel electrophoresis followed by protein staining or Western blot analysis.

"Antibody of the invention" or other similar term refers to whole immunoglobulin as well immunologically active fragments which bind native TF. The immunoglobulins and immunologically active fragments thereof include an antibody binding site (i.e., peritope capable of specifically binding native human TF). Exemplary antibody fragments include, for example, Fab, F(v), Fab', F(ab')$_2$ fragments, "half molecules" derived by reducing the disulfide bonds of immunoglobulins, single chain immunoglobulins, or other suitable antigen binding fragments (see e.g., Bird et al., *Science,* pp. 242–424 (1988); Huston et al., *PNAS, (USA),* 85:5879 (1988); Webber et al., *Mol. Immunol.,* 32:249 (1995)). The antibody or immunologically active fragment thereof may be of animal (e.g., a rodent such as a mouse or a rat), or chimeric form (see Morrison et al., *PNAS,* 81:6851 (1984); Jones et al., *Nature,* pp. 321, 522 (1986)). Single chain antibodies of the invention can be preferred.

Similarly, a "nucleic acid of the invention" refers to a sequence which can be expressed to provide an antibody of the invention as such term is specified to mean immediately above.

As discussed above, antibodies of the invention can be administered to a mammal, preferably a primate such as a human, to prevent or reduce thromboses such as restenosis, typically in a composition including one or more pharmaceutically acceptable non-toxic carriers such as sterile water or saline, glycols such as polyethylene glycol, oils of vegetable origin, and the like. In particular, biocompatible, biodegradable lactide polymer, lactide glycolide copolymer or polyoxyethylene, polyoxypropylene copolymers may be useful excipients to control the release of the antibody-containing compositions described herein. Other potentially useful administration systems include ethylene vinyl acetate copolymer particles, osmotic pumps, and implantable infusion systems and liposomes. Generally, an anti-coagulant composition of the invention will be in the form of a solution or suspension, and will preferably include approximately 0.01% to 10% (w/w) of the antibody of the present invention, preferably approximately 0.01% to 5% (w/w) of the antibody. The antibody can be administered as a sole active ingredient in the composition, or as a cocktail including one or more other anti-coagulant (e.g., heparin, hirudin, or hirulog), anti-platelet (e.g., ReoPro), or thrombolytic agents (e.g., tissue plasminogen activator, strepokinase and urokinase). Additionally, antibodies of the invention can be administered prior to, or after administration of one or more suitable anti-coagulant, anti-platelet or thrombolytic agents to boost or prolong desired anti-coagulation activity.

As also discussed above, antibodies of the invention can be employed to reduce potential blood coagulation arising from use of medical implementation, e.g. an indwelling device such as a catheter, stent, etc. In one preferred method, the implementation can be treated with an antibody of the invention (e.g., as a 1 mg/ml saline solution) prior to contact with a body fluid. Alternatively, or in addition, an antibody of the invention can be combined with the body fluid in an amount sufficient to minimize blood clotting.

Therapeutic anti-coagulant compositions according to the invention are suitable for use in parenteral or intravenous administration, particularly in the form of liquid solutions. Such compositions may be conveniently administered in unit dose and may be prepared in accordance with methods known in the pharmaceutical art. See *Remington's Pharmaceutical Sciences,* (Mack Publishing Co., Easton Pa., (1980)). By the term "unit dose" is meant a therapeutic composition of the present invention employed in a physically discrete unit suitable as unitary dosages for a primate such as a human, each unit containing a pre-determined quantity of active material calculated to produce the desired therapeutic effect in association with the required diluent or carrier. The unit dose will depend on a variety of factors including the type and severity of thrombosis to be treated, capacity of the subject's blood coagulation system to utilize the antibody, and degree of inhibition or neutralization of FX activation desired. Precise amounts of the antibody to be administered typically will be guided by judgement of the practitioner, however, the unit dose will generally depend on the route of administration and be in the range of 10 ng/kg body weight to 50 mg/kg body weight per day, more typically in the range of 100 ng/kg body weight to about 10 mg/kg body weight per day. Suitable regiments for initial administration in booster shots are also variable but are typified by an initial administration followed by repeated doses at one or more hour intervals by a subsequent injection or other administration. Alternatively, continuous or intermittent intravenous infusions may be made sufficient to maintain concentrations of at least from about 10 nanomolar to 10 micromolar of the antibody in the blood.

In some instances, it may be desirable to modify the antibody of the present invention to impart a desirable biological, chemical or physical property thereto. More particularly, it may be useful to conjugate (i.e. covalently link) the antibody to a pharmaceutical agent, e.g. a fibrinolytic drug such as t-PA, streptokinase, or urokinase to provide fibrinolytic activity. Such linkage can be accomplished by several methods including use of a linking molecule such as a heterobifunctional protein cross-linking agent, e.g. SPDP, carbodimide, or the like, or by recombinant methods.

In addition to pharmaceuticals such as a fibrinolytic agent, an antibody of the invention can be conjugated to a toxin of e.g. plant or bacterial origin such as diphtheria toxin (i.e., DT), shiga toxin, abrin, cholera toxin, ricin, saporin, pseudomonas exotoxin (PE), pokeweed antiviral protein, or gelonin. Biologically active fragments of such toxins are well known in the art and include, e.g., DTA chain and ricin A chain. The toxin can also be an agent active at cell surfaces such as phospholipases (e.g., phospholipase C). As another example, the toxin can be a chemotherapeutic drug such as, e.g., vendesine, vincristine, vinblastin, methotrexate, adriamycin, bleomycin, or cisplatin, or, the toxin can be a radionuclide such as, e.g., iodine-131, yttrium-90, rhenium-188 or bismuth-212 (see generally, Moskaug et al., *J. Biol. Chem.*, 264:15709 (1989); I. Pastan et al., *Cell*, 47:641 (1986); Pastan et al., *Recombinant Toxins as Novel Therapeutic Agents, Ann. Rev. Biochem.*, 61:331 (1992); *Chimeric Toxins Olsnes and Phil, Pharmac. Ther.*, 25:355 (1982); published PCT Application No. WO 94/29350; published PCT Application No. WO 94/04689; and U.S. Pat. No. 5,620,939). Also, as discussed above, in addition to a toxin, an antibody of the invention can be conjugated to an effector molecule (e.g. IgG1 or IgG3) to provide complement-fixing ability and antibody-dependent cell-mediated cytoxicity upon administration to a mammal.

Such an antibody/cytotoxin or effector molecule conjugate can be administered in a therapeutically effective amount to a mammal, preferably a primate such as a human, where the mammal is known to have or is suspected of having tumor cells, immune system cells, or endothelia capable of expressing TF. Exemplary of such tumor cells, immune system cells and endothelia include malignancies of the breast and lung, monocytes and vascular endothelia.

Antibodies of the invention also can be conjugated to a variety of other pharmaceutical agents in addition to those described above such as, e.g., drugs, enzymes, hormones, chelating agents capable of binding a radionuclide, as well as other proteins and polypeptides useful for diagnosis or treatment of disease. For diagnostic purposes, the antibody of the present invention can be used either detectably-labelled or unlabelled. For example, a wide variety of labels may be suitably employed to detectably-label the antibody, such as radionuclides, fluors, enzymes, enzyme substrates, enzyme cofactors, enzyme inhibitors, ligands such as, e.g., haptens, and the like.

Diagnostic methods are also provided including in vivo diagnostic imaging [see, e.g., A. K. Abbas, *Cellular and Molecular Immunology*, pg. 328 (W. B. Saunders Co. 1991)]. For most in vivo imaging applications, an antibody of the invention can be detectably-labeled with, e.g., $^{125}I$, $^{32}P$, $^{99}Tc$, or other detectable tag, and subsequently administered to a mammal, particularly a human, for a predetermined amount of time sufficient to allow the antibody to contact a desired target. The subject is then scanned by known procedures such as scintigraphic camera analysis to detect binding of the antibody. The analysis could aid in the diagnosis and treatment of a number of thromboses such as those specifically disclosed herein. The method is particularly useful when employed in conjunction with cardiac surgery, particularly angioplasty, or other surgical procedure where undesired formation of a blood clot can occur, to visualize the development or movement of a blood clot.

Antibodies of the invention also can be used to prepare substantially pure (e.g., at least about 90% pure, preferably at least about 96 or 97% pure) native TF, particularly native human TF from a biological sample. For example, native TF can be obtained as previously described (see e.g., L. V. M. Rao et al., *Thrombosis Res.*, 56:109 (1989)) and purified by admixing the solution with a solid support comprising the antibody to form a coupling reaction admixture. Exemplary solid supports include a wall of a plate such as a microtitre plate, as well as supports including or consisting of polystyrene, polyvinylchloride, a cross-linked dextran such as Sephadex™ (Pharmacia Fine Chemicals), agarose, polystyrene beads (Abbott Laboratories), polyvinyl chloride, polystyrene, polyacrylmide in cross-linked form, nitrocellulose or nylon and the like. The TF can then be isolated from the solid support in substantially pure form in accordance with standard immunological techniques. See generally Harlow and Lane supra and Ausubel et al. supra).

As also discussed above, antibodies of the invention can be employed to detect native human TF in a biological sample, particularly native TF associated with a blood clot. Exemplary biological samples include blood plasma, serum, saliva, urine, stool, vaginal secretions, bile, lymph, ocular humors, cerebrospinal fluid, cell culture media, and tissue, particularly vascular tissues such as cardiac tissue. Samples may be suitably obtained from a mammal suffering from or suspected of suffering from a thrombosis, preferably restenosis, associated with, e.g., an invasive medical procedure such as cardiopulmonary bypass surgery; a heart ailment such as myocardial infarction, cardiomyopathy, valvular heart disease, unstable angina, or artrial fibrillation associated with embolization; a coagulopathy including disseminated intravascular coagulation, deployment of an implementation such as a stent or catheter; shock (e.g., septic shock syndrome), vascular trauma, liver disease, heat stroke, malignancies (e.g., pancreatic, ovarian, or small lung cell carcinoma), lupus, eclampsia, perivascular occlusive disease, and renal disease.

For such assays, an antibody of the invention can be detectably-labelled with a suitable atom or molecule e.g., radioactive iodine, tritium, biotin, or reagent capable of generating a detectable product such as an anti-iodiotypic antibody attached to an enzyme such as β-galactosidase or horseradish peroxidase, or a fluorescent tag (e.g., fluorescein or rhodamine) in accordance with known methods. After contacting the biological sample with the detectably-labelled antibody, any unreacted antibody can be separated from the biological sample, the label (or product) is detected by conventional immunological methods including antibody capture assay, antibody sandwich assay, RIA, ELISA, immunoprecipitation, immunoabsorption and the like (see Harlow and Lane, supra; Ausubel et al. supra). Any label (or product) in excess of that detected in a suitable control sample is indicative of the presence of native TF, more particularly a blood clot, in the biological sample. For example, antibodies of the invention can be detectably-labelled to detect, and preferably quantitate, native TF in accordance with standard immunological techniques such as antibody capture assay, ELISA, antibody sandwich assay, RIA, immunoprecipitation, immunoabsorption and the like. In some cases, particularly when a tissue is used, the immunological technique may include tissue fixation with a reagent known to substantially maintain protein conformation (e.g., dilute formaldehyde). See generally, Ausubel et al., *Current Protocols in Molecular Biology*, John Wiley & Sons, New York, (1989); Harlow and Lane in *Antibodies: A Laboratory Manual*, CSH Publications, NY (1988).

Antibodies of the invention also can be used for detecting and purifying cells which express native TF, including fibroblasts, brain cells, immune cells, (e.g., monocytes), epithelia, as well as certain malignant cells. Preferred methods of detecting and purifying the cells include conventional immunological methods (e.g., flow cytometry methods such as FACS, and immunopanning). Substantially pure populations of cells expressing native TF are useful in clinical and research settings, e.g., to establish such cells as cultured cells for screening TF-binding antibodies.

The invention also provides test and diagnostic kits for detection of native TF, particularly native human TF, in a test sample, especially a body fluid such as blood, plasma, etc., or tissue as discussed above. A preferred kit includes a detectably-labelled antibody of the invention. The diagnostic kit can be used in any acceptable immunological format such as an ELISA format to detect the presence or quantity of native TF in the biological sample.

All documents mentioned herein are fully incorporated by reference in their entirety.

The following non-limiting examples are illustrative of the invention. In the following examples and elsewhere the antibodies H36 and H36.D2 are referred to. Those antibodies are the same antibody as H36.D2.B7, but H36 is derived from the mother clone, and H36.D2 is obtained from the primary clone, whereas H36.D2.B7 is obtained from the secondary clone. No differences have been observed between those three clones with respect to ability to inhibit TF or other physical properties.

EXAMPLE 1

Preparation and Cloning of Anti-rhTF Monoclonal Antibodies

Monoclonal antibodies against rhTF were prepared as follows.

A. Immunization and Boosts

Five female BALB/c mice were immunized with 10 µg each of lipidated, purified rhTF. The mice were initially sensitized intraperitoneally using Hunter's Titermax adjuvant. Three final boosts were administered in 0.85% NaCl. Boosts were 2, 5.5, and 6.5 months post initial sensitization. All boosts were given intraperitoneally, except the first which was subcutaneous. The final boost was given 3 days pre-fusion and 20 µg was administered.

B. Fusion of Mouse Spleen Lymphocytes with Mouse Myeloma Cells

Lymphocytes from the spleen of one rhTF immunized BALB/c mouse was fused to X63-Ag8.653 mouse myeloma cells using PEG 1500. Following exposure to the PEG, the cells were incubated for one hour in heat inactivated fetal bovine serum at 37° C. The fused cells were then resuspended in RPMI 1640 and incubated overnight at 37° C. with 10% $CO_2$. The cells were plated the next day using RPMI 1640 and supplemented with macrophage culture supernatant.

C. ELISA Development

Plates for the ELISA assay were coated with 100 microliters of recombinant tissue factor (0.25 µg/ml) in a carbonate based buffer. All steps were performed at room temperature. Plates were blocked with BSA, washed, and then the test samples and controls were added. Antigen/antibody binding was detected by incubating the plate with goat anti-mouse HRP conjugate (Jackson ImmunoResearch Laboratories) and then using an ABTS peroxidase substrate system (Kirkegaad and Perry Laboratories). Absorbance were read on an automatic plate reader at a wavelength of 405 nm.

D. Stabilization of rhTF Hybridoma Cell Lines

Two weeks after fusion, screening of hybridoma colonies by specific rhTF ELISA was started. Screening for new colonies continued for three weeks. The positive clones were tested every one to two weeks for continued antibody production until fifteen stable clones were frozen down.

E. Primary and Secondary Cloning

Limiting dilution cloning was performed on each of the positive stable hybridomas to obtain primary clones. The cells were thawed, grown in culture for a short period of time, and then diluted from 10 cells/well to 0.1 cells/well. Primary clones were tested by anti-rhTF ELISA and five to six positive clones were expanded and frozen.

Secondary clone of anti-rhTF antibody, H36.D2.B7, was obtained from primary clone, H36.D2, prepared and stored in liquid nitrogen as described above. Four different dilutions, 5 cells/well, 2 cells/well, 1 cell/well, 0.5 cells/well of the primary clone were prepared in 96-wells microtiter plates to start the secondary cloning. Cells were diluted in IMDM tissue culture media containing the following additives: 20% fetal bovine serum (FBS), 2 mM L-glutamine, 100 units/ml of penicillin, 100 µg/ml of streptomycin, 1% GMS-S, 0.075% $NaHCO_3$. To determine clones that secrete anti-rhTF antibody, supernatants from five individual wells of the 0.2 cells/well microtiter plate were withdrawn after two weeks of growth and tested for the presence of anti-rhTF antibody by ELISA assays as described above. All five clones showed positive results in the ELISA assay, with H36.D2.B7 being the best antibody producer. All five clones were adapted and expanded in RPMI media containing the following additive: 10% FBS, 2 mM L-glutamine, 100 units/ml of penicillin, 100 µg/ml of streptomycin, 1% GMS-S, 0.075% $NaHCO_3$, and 0.013 mg/ml of oxalaacetic acid. H36.D2.B7 was purified by Protein A affinity chromatography from the supernatant of cell culture and was tested for its ability to inhibit TF:VIIa in a FX activation assay. The results indicated that H36.D2.B7 had the same inhibition as H36.D2 antibody. All cells were stored in liquid nitrogen.

F. Isolation of total RNA from H36.D2.B37

269 µg of total RNA was isolated from $2.7 \times 10^5$ H36.D2.B7 hybridoma cells. The isolation of total RNA was performed as described in the RNeasy Midi Kits protocol from Qiagen. The RNA sample was stored in water at −20° C. until needed.

G. cDNA Synthesis and Cloning of Variable Regions of H36.D2.B7 Gene

To obtain the first strand of cDNA, a reaction mixture containing 5 µg of total RNA isolated as above, back primers JS300 (all primers are identified below) for the heavy chain (HC) and OKA 57 for the light chain (LC), RNase inhibitor, dNTP's, DTT, and superscript II reverse transcriptase, was prepared and incubated at 42° C. for 1 hour. The reaction tube is then incubated at 65 ° C. for 15 minutes to stop the transcription. After cooling down, five units of RNase H was then added and the reaction was allowed to incubate at 37° C. for 20 minutes. The cDNA sample was stored at −70° C. until needed.

PCR (polymerase chain reaction) was conducted separately to clone the variable regions of both HC and LC of anti-rhTF, H36.D2.B7 from the cDNA made as above (nucleic acid and amino acid sequences of those HC and LC variable regions set forth in FIGS. 1A and 1B). Three rounds of PCR were conducted. Round 1: PCR was run for 35 cycles at 96° C., 53° C. and 72° C. using front primer JS002 and back primer JS300 for HC. For LC front primer JS009 and back primer OKA 57 were used and PCR was run for 35 cycles at 96° C., 63° C. and 72° C. Round 2: PCR of both HC and LC was run the same as in Round 1 with the exception that pMC-18 was used for HC front primer and pMC-15 for LC front primer. Round 3: PCR was run for 30 cycles at 96° C., 60–65° C. and 72° C. using H36HCF and H36HCR primers for HC. For LC, PCR was run for 30 cycles at 96° C., 58° C. and 72° C. using H36LCF and H36LCR primers.

The following primers were used for cloning H36.D2.B7 variable regions of HC and LC.

```
OKA 57:
5'-GCACCTCCAGATGTTAACTGCTC-3'                                       (SEQ ID NO:17)

JS300:
5'-GAARTAVCCCTTGACCAGGC-3'                                          (SEQ ID NO:18)

JS009:
5'-GGAGGCGGCGGTTCTGACATTGTGMTGWCMCART-3'                            (SEQ ID NO:19)

JS002:
5'-ATTTCAGGCCCAGCCGGCCATGGCCGARGTYCARCTKCARCARYC-3'                 (SEQ ID NO:20)

pMC-15:
5'-CCCGGGCCACCATGKCCCCWRCTCAGYTYCTKG-3'                             (SEQ ID NO:21)

pMC-18:
5'-CCCGGGCCACCATGGRATGSAGCTGKGTMATSCTC-3'                           (SEQ ID NO:22)

H36HCF:
5'-ATATACTCGCGACAGCTACAGGTGTCCACTCCGAGATCCAGCTGCAGCAGTC-3'          (SEQ ID NO:23)

H36HCR:
5'-GACCTGAATTCTAAGGAGACTGTGAGAGTGG-3'                               (SEQ ID NO:24)

H36LCF:
5'-TTAATTGATATCCAGATGACCCAGTCTCC-3'                                 (SEQ ID NO:25)

H36LCR:
TAATCGTTCGAAAAGTGTACTTACGTTTCAGCTCCAGCTTGGTCC                       (SEQ ID NO:26)
``` where in the above SEQ ID NOS: 17 through 26: K is G or T; M is A or C; R is A or G; S is C or G; V is A, C or G; W is A or T; Y is C or T.

EXAMPLE 2

Binding Activity of Mabs of the Invention

Mabs of the invention as prepared in Example 1 above were employed. The rhTF molecule was expressed in *E. coli* and purified by immunoaffinity chromatography in accordance with standard methods (see Harlow and Lane, supra, Ausubel et al. supra). Mab association ($K_a$) and dissociation ($K_d$) constants were determined by ELISA and surface plasmon resonance (i.e., BIACore) assays (see e.g., Harlow and Lane, supra; Ausubel et al. supra; Altschuh et al., *Biochem.*, 31:6298 (1992); and the BIAcore method disclosed by Pharmacia Biosensor). For BIACore assays, rhTF was immobilized on a biosensor chip in accordance with the manufacturer's instructions. Constants for each Mab were determined at four antibody concentrations (0.125 nM, 0.25 nM, 0.5 nM, and 1 nM).

Protein concentrations were determined by standard assay (M. M. Bradford, *Anal. Biochem.*, 72:248 (1976)) using Bovine Serum Albumin as a standard and a commercially available dye reagent (Bio-Rad).

FIG. 2 shows association and disassociation constants for each anti-rhTF Mab. Mab H36 exhibited the highest association rate ($K_a = 3.1 \times 10^{-10}$ M$^{-1}$) and the lowest disassociation rate ($K_d = 3.2 \times 10^{-11}$ M) of any of the anti-rhTF Mabs tested.

EXAMPLE 3

FXa-specific Substrate Assay

In general, the experiments described herein were conducted using rhTF lipidated with phosphatidycholine (0.07 mg/ml) and phosphatidylserine (0.03 mg/ml) at a 70/30 w/w ratio in 50 mM Tris-HCl, pH 7.5, 0.1% bovine serum albumin (BSA) for 30 minutes at 37° C. A stock solution of preformed TF:VIIa complex was made by incubating 5 nM of the lipidated rhTF and 5 nM of FVIIa for 30 minutes at 37° C. The TF:VIIa complex was aliquoted and stored at −70° C. until needed. Purified human factors VII, VIIa, and FX were obtained from Enyzme Research Laboratories, Inc. The following buffer was used for all FXa and FVIIa assays: 25 mM Hepes-NaOH, 5 mM CaCl$_2$, 150 mM NaCl, 0.1% BSA, pH 7.5.

Mabs were screened for capacity to block TF:VIIa-mediated activation of FX to FXa. The FX activation was determined in two discontinuous steps. In the first step (FX activation), FX conversion to FXa was assayed in the presence of Ca$^{+2}$. In the second step (FXa activity assay), FX activation was quenched by EDTA and the formation of FXa was determined using a FXa-specific chromogenic substrate (S-2222). The S-2222 and S-2288 (see below) chromogens were obtained from Chromogenix (distributed by Pharmacia Hepar Inc.). FX activation was conducted in 1.5 ml microfuge tubes by incubating the reaction with 0.08 nM TF:VIIa, either pre-incubated with an anti-rhTF antibody or a buffer control. The reaction was subsequently incubated for 30 minutes at 37° C., then 30 nM FX was added followed by an additional incubation for 10 minutes at 37° C. FXa activity was determined in 96-well titre plates. Twenty microlitres of sample was withdrawn from step one and admixed with an equal volume of EDTA (500 mM) in each well, followed by addition of 0.144 ml of buffer and 0.016 ml of 5 mM S-2222 substrate. The reaction was allowed to incubate for an additional 15–30 minutes at 37° C. Reactions were then quenched with 0.05 ml of 50% acetic acid, after which, absorbance at 405 nm was recorded for each reaction. The inhibition of TF:VIIa activity was calculated from $OD_{405nm}$ values in the experimental (plus antibody) and control (no antibody) samples. In some experiments, an anti-hTF antibody, TF/VIIa, and FX were each added simultaneously to detect binding competition. FIG. 3 shows that the H36.D2 MAb (in bold) inhibited TF:/VIIa activity toward FX to a significantly greater extent (95%) than other anti-rHTF Mabs tested.

EXAMPLE 4

FVIIa-Specific Substrate Assay

Mabs were further screened by an FVIIa specific assay. In this assay, 5 nM lipidated rhTF was first incubated with buffer (control) or 50 nM antibody (experimental) in a 96-well titre plate for 30 minutes at 37° C., then admixed with 5 nM purified human FVIIa ($V_T$=0.192 ml), followed by 30 minutes incubation at 37° C. Eight microliters of a 20 mM stock solution of the FVIIa specific substrate S-2288 was then added to each well (final concentration, 0.8 mM). Subsequently, the reaction was incubated for one hour at 37° C. Absorbance at 405 nm was then measured after quenching with 0.06 ml of 50% acetic acid. Percent inhibition of TF/VIIa activity was calculated from $OD_{405nm}$ values from the experimental and control samples.

FIG. 4 shows the H36 antibody did not significantly block TF/VIIa activity toward the S-2288 substrate when the antibody was either pre-incubated with TF (prior to VIIa addition) or added to TF pre-incubated with VIIa (prior to adding the antibody). This indicates that H36 does not interfere with the interaction (binding) between TF and FVIIa, and that H36 also does not inhibit TF:VIIa activity toward a peptide substrate.

EXAMPLE 5

Prothrombin Time (PT) Assay

Calcified blood plasma will clot within a few seconds after addition of thromboplastin (TF); a phenomenon called the "prothrombin time" (PT). A prolonged PT is typically a useful indicator of anti-coagulation activity (see e.g., Gilman et al. supra).

The H36.D2 antibody was investigated for capacity to affect PT according to standard methods using commercially available human plasma (Ci-Trol Control, Level I obtained from Baxter Diagnostics Inc.). Clot reactions were initiated by addition of lipidated rhTF in the presence of $Ca^{++}$. Clot time was monitored by an automated coagulation timer (MLA Electra 800). PT assays were initiated by injecting 0.2 ml of lipidated rhTF (in a buffer of 50 mM Tris-HCl, pH 7.5, containing 0.1% BSA, 14.6 mM $CaCl_2$, 0.07 mg/ml of phosphatidylcholine, and 0.03 mg/ml of phosphatidylserine) into plastic twin-well cuvettes. The cuvettes each contained 0.1 ml of the plasma preincubated with either 0.01 ml of buffer (control sample) or antibody (experimental sample) for 1–2 minutes. The inhibition of TF-mediated coagulation by the H36.D2 antibody was calculated using a TF standard curve in which the log [TF] was plotted against log clot time.

FIG. 5 shows the H36.D2 antibody substantially inhibits TF-initiated coagulation in human plasma. The H36.D2 antibody increased PT times significantly, showing that the antibody is an effective inhibitor of TF-initiated coagulation (up to approximately 99% inhibition).

EXAMPLE 6

FX and the H36.D2 Antibody Compete For Binding to the TF:VIIa Complex

Competition experiments were conducted between TF/VIIa, FX and the H36.D2 antibody. FIG. 6A illustrates the results of an experiment in which a preformed TF/VIIa complex (0.08 nM) was pre-incubated at 37° C. for 30 minutes in buffer including 0.02 nM, 0.04 nM, 0.08 nM and 0.16 nM of the H36.D2 monoclonal antibody, respectively. FX (30 nM) was then added to the TF/VIIa and H36.D2 antibody mixture and the mixture allowed to incubate for an additional 10 minutes at 37° C. FX activation was quenched with EDTA as described previously. The FXa produced thereby was determined by the FXa-specific assay described in Example 3, above.

Figure 6B:
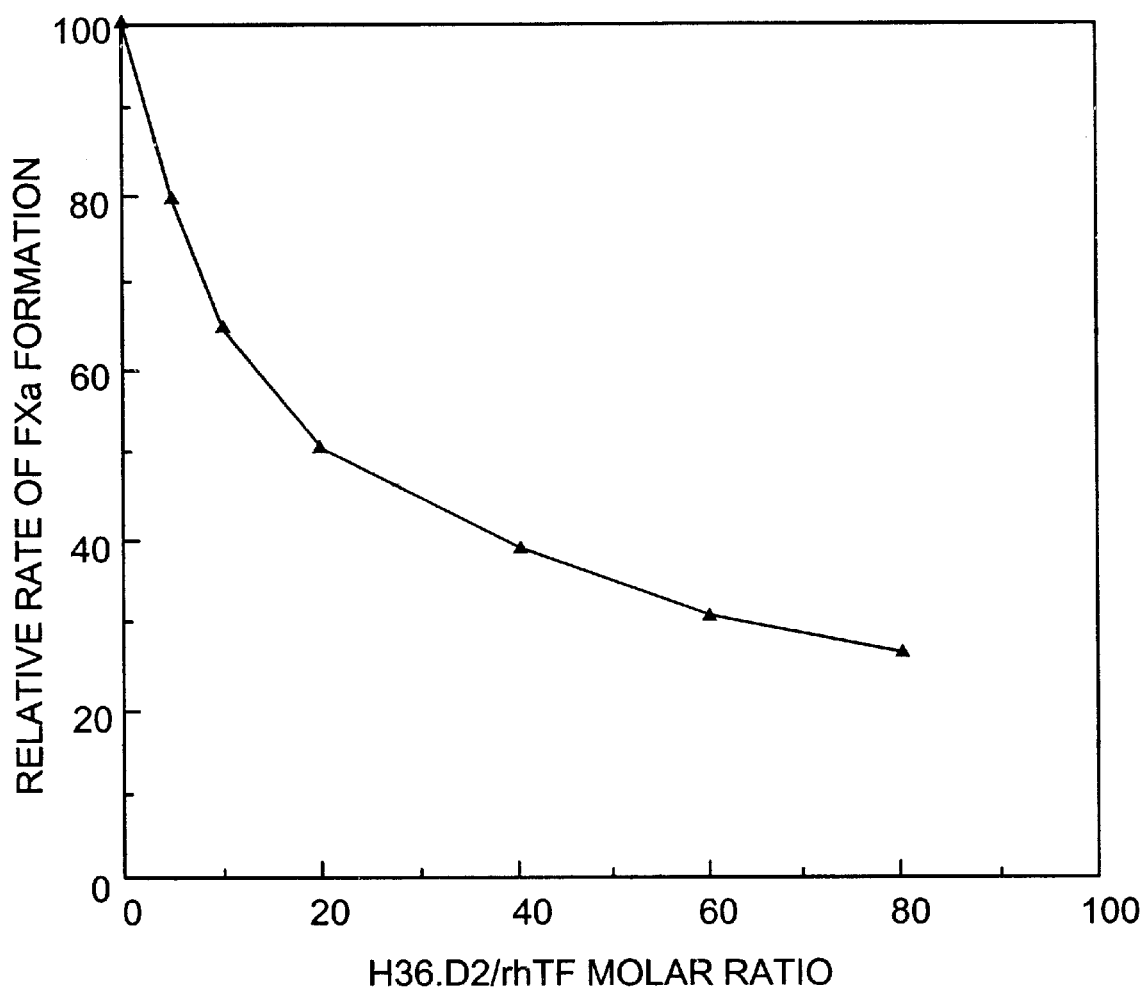

FIG. 6B shows the results of an experiment conducted along the lines just-described, except that the H36.D2 antibody, pre-formed TF:VIIa, and FX were added simultaneously to start the FX activation assay.

The data set forth in FIGS. 6A and 6B show that the H36.D2 antibody and FX compete for binding to the pre-formed TF/VIIa complex.

EXAMPLE 7

Inhibition of TF Activity in Cell Culture

J-82 is a human bladder carcinoma cell line (available from the ATCC) which abundantly expresses native human TF as a cell surface protein. To see if the H36.D2 antibody could prevent FX from binding to native TF displayed on the cell surface, a J-82 FX activation assay was conducted in microtitre plates in the presence of FVII (see D. S. Fair et al., J. Biol. Chem., 262:11692 (1987)). To each well, $2 \times 10^5$ cells was added and incubated with either 50 ng FVII, buffer (control sample) or the anti-TF antibody (experimental sample) for 2 hours at 37° C. Afterwards, each well was gently washed with buffer and 0.3 ml of FX (0.05 mg/ml) was added to each well for 30 minutes at room temperature. In some cases, the antibody was added at the same time as FX to detect binding competition for the native TF. Thereafter, 0.05 ml aliquots were removed and added to new wells in a 96-well titre plate containing 0.025 ml of 100 mM EDTA. FXa activity was determined by the FXa-specific assay as described in Example 3, above. Inhibition of TF activity on the surface of the J-82 cells was calculated from the $OD_{405nm}$ in the absence (control sample) and presence of antibody (experimental sample).

FIG. 7 shows that the H36.D2 antibody bound native TF expressed on J-82 cell membranes and inhibited TF-mediated activation of FX. These results indicate that the antibody competes with FX for binding to native TF displayed on the cell surface. Taken with the data of Example 8, below, the results also show that the H36.D2 antibody can bind a conformational epitope on native TF in a cell membrane.

EXAMPLE 8

Specific Binding of the H36.D2 Antibody to Native rhTF

Evaluation of H36.D2 binding to native and non-native rhTF was performed by a simplified dot blot assay. Specifically, rhTF was diluted to 30 μg/ml in each of the following three buffers: 10 mM Tris-HCl, pH 8.0; 10 mM Tris-HCl, pH 8.0 and 8 M urea; and 10 mM Tris-HCl, pH 8.0, 8 M urea and 5 mM dithiothreitol. Incubation in the Tris buffer maintains rhTF in native form, whereas treatment with 8M urea and 5 nM dithiothreitol produces non-native (denatured) rhTF. Each sample was incubated for 24 hours at room temperature. After the incubation, a Millipore Immobilon (7×7 cm section) membrane was pre-wetted with methanol, followed by 25 mM Tris, pH 10.4, including 20% methanol. After the membranes were air-dried, approximately 0.5 µl, 1 µl, and 2 µl of each sample (30 µg/ml) was applied to the membrane and air-dried. After blocking the membrane by PBS containing 5% (w/v) skim milk and 5% (v/v) NP-40, the membrane was probed with H36.D2 antibody, followed by incubation with a goat anti-mouse IgG peroxidase conjugate (obtained from Jackson ImmunoResearch Laboratories, Inc.). After incubation with ECL Western Blotting reagents in accordance with the manufacturer's instructions (Amersham), the membrane was wrapped with plastic film (Saran Wrap) and exposed to X-ray film for various times.

FIG. 8A shows that the H36.D2 Mab binds a conformational epitope on native TF in the presence of Tris buffer or Tris buffer with 8M urea (lanes 1 and 2). The autoradiogram was exposed for 40 seconds. However, when the native TF was denatured with 8M urea and 5 mM DTT, H36.D2 binding was significantly reduced or eliminated (lane 3).

FIG. 8B shows an over-exposed autoradiogram showing residual binding of the H36.D2 antibody to non-native (i.e., denatured) rhTF. The over-exposure was for approximately 120 seconds. Treatment with 8M urea alone probably resulted in only partial denaturation of the native rhTF since the two disulfide bonds in TF are not reduced. It is also possible that the partially denatured TF may refold back to native confirmation during later blotting process when urea is removed. These results also clearly distinguish preferred antibodies of the invention which do not bind denatured TF from previously reported antibodies which do not selectively bind to a conformational epitope and bind to denatured TF (see U.S. Pat. No. 5,437,864 where in FIG. 18 Western Blot analysis shows binding to TF denatured by SDS).

The invention has been described in detail with reference to preferred embodiments thereof. However, it will be appreciated that those skilled in the art, upon consideration of the disclosure, may make modification and improvements within the spirit and scope of the invention.

What is claimed is:

1. An antibody that binds native human tissue factor to form a complex whereby factor X binding to the complex is inhibited, wherein the antibody is chimeric and comprises a constant region of human origin.

2. An antibody of claim 1 wherein the antibody is a single chain antibody.

3. An antibody of claim 1 wherein the antibody comprises hypervariable regions that have at least 90 percent sequence identity to SEQ ID NOS. 5 through 10 inclusive.

4. An antibody of claim 1 wherein the antibody comprises hypervariable regions represented by SEQ ID NOS. 5 through 10 inclusive.

5. An antibody of claim 1 wherein the antibody has a binding specificity for native human tissue factor about equal to or greater than the antibody obtained from H36.D2.B7 deposited under ATCC Accession No. HB-12255.

6. An antibody of claim 1 having the binding affinity for native human tissue factor about equal to or greater than H36.D2.B7 deposited under ATCC Accession No. HB-12255.

7. A method of detecting tissue factor in a biological sample comprising:

contacting a biological sample with an antibody of claim 1, and detecting binding of the antibody to thereby assess the presence of tissue factor in the biological sample.

8. The antibody of claim 1 wherein the antibody is monoclonal.

9. An antibody of claim 1 that is an immunologically active antibody fragment.

10. An antibody of claim 1 that is a Fab, F(v), Fab', or F(ab')$_2$.

11. An antibody of claim 1 that binds with native tissue factor whereby Factor X activity to the complex is inhibited by at least 80 percent in a standard in vitro binding assay.

12. An antibody of claim 1 that binds with native tissue factor whereby Factor X binding to the complex is inhibited by at least 90 percent in a standard in vitro binding assay.

13. An antibody of claim 1 that binds with native tissue factor whereby Factor X binding to the complex is inhibited by at least 95 percent in a standard in vitro binding assay.

14. An antibody that binds native human tissue factor to form a complex whereby factor X binding to the complex is inhibited, wherein the antibody is chimeric and comprises a constant region of human origin, the antibody comprising hypervariable region represented SEQ ID NOS. 5 through 10 inclusive.

15. An antibody that binds native human tissue factor to form a complex whereby factor X binding to the complex is inhibited.

16. An antibody of claim 15 wherein the antibody is a single chain antibody.

17. An antibody of claim 15 wherein the antibody comprises hypervariable regions that have at least 90 percent sequence identity to SEQ ID NOS. 5 through 10 inclusive.

18. An antibody of claim 15 wherein the antibody comprises hypervariable regions represented by SEQ ID NOS. 5 through 10 inclusive.

19. An antibody of claim 15 wherein the antibody has a binding specificity for native tissue factor about equal to or greater than the antibody obtained from H36.D2.B7 deposited under ATCC Accession No. HB-12255.

20. An antibody of claim 15 having the binding affinity for native human tissue factor about equal to or greater than H36.D2.B7 deposited under ATCC Accession No. HB-12255.

21. The antibody of claim 15 wherein the antibody is monoclonal.

22. An antibody of claim 15 that is an immunologically active antibody fragment.

23. An antibody of claim 15 that is a Fab, F(v), Fab', or F(ab')$_2$.

24. An antibody of claim 15 that binds with native tissue factor whereby Factor X activity to the complex is inhibited by at least 80 percent in a standard in vitro binding assay.

25. An antibody of claim 15 that binds with native tissue factor whereby Factor X binding to the complex is inhibited by at least 90 percent in a standard in vitro binding assay.

26. An antibody of claim 15 that binds with native tissue factor whereby Factor X binding to the complex is inhibited by at least 95 percent in a standard in vitro binding assay.

27. A method of detecting human tissue factor in a biological sample comprising:

contacting a biological sample with an antibody of claim 15, and detecting binding of the antibody to thereby assess the presence of tissue factor in the biological sample.

28. An humanized chimeric antibody that binds native human tissue factor to form a complex whereby factor X binding to the complex is inhibited.

29. An antibody of claim 28 wherein the antibody comprises hypervariable regions that have at least 90 percent sequence identity to SEQ ID NOS. 5 through 10 inclusive.

30. An antibody of claim 28 wherein the antibody comprises hypervariable regions represented by SEQ ID NOS. 5 through 10 inclusive.

31. An antibody of claim 28 wherein the antibody has a binding specificity for native tissue factor about equal to or greater than the antibody obtained from H36.D2.B7 deposited under ATCC Accession No. HB-12255.

32. An antibody of claim 28 having the binding affinity for native human tissue factor about equal to or greater than H36.D2.B7 deposited under ATCC Accession No. HB-12255.

33. An antibody of claim 28 wherein the antibody comprises human variable regions.

34. The antibody of claim 28 wherein the antibody is monoclonal.

35. An antibody of claim 28 that is an immunologically active antibody fragment.

36. An antibody of claim 28 that is a Fab, F(v), Fab', or F(ab')$_2$.

37. An antibody of claim 28 that binds with native tissue factor whereby Factor X activity to the complex is inhibited by at least 80 percent in a standard in vitro binding assay.

38. An antibody of claim 28 that binds with native tissue factor whereby Factor X binding to the complex is inhibited by at least 90 percent in a standard in vitro binding assay.

39. An antibody of claim 29 that binds with native tissue factor whereby Factor X binding to the complex is inhibited by at least 95 percent in a standard in vitro binding assay.

40. A method of detecting human tissue factor in a biological sample comprising:

contacting a biological sample with an antibody of claim 28, and detecting binding of the antibody to thereby assess the presence of tissue factor in the biological sample.

* * * * *

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
         (A) LENGTH: 321 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 1:

```
GACATTCAGA TGACCCAGTC TCCTGCCTCC CAGTCTGCAT CTCTGGGAGA AAGTGTCACC      60

ATCACATGCC TGGCAAGTCA GACCATTGAT ACATGGTTAG CATGGTATCA GCAGAAACCA     120

GGGAAATCTC CTCAGCTCCT GATTTATGCT GCCACCAACT TGGCAGATGG GGTCCCATCA     180

AGGTTCAGTG GCAGTGGATC TGGCACAAAA TTTTCTTTCA AGATCAGCAG CCTACAGGCT     240

GAAGATTTTG TAAATTATTA CTGTCAACAA GTTTACAGTT CTCCATTCAC GTTCGGTGCT     300

GGGACCAAGC TGGAGCTGAA A                                              321
```

(2) INFORMATION FOR SEQ ID NO: 2:

(i) SEQUENCE CHARACTERISTICS:
         (A) LENGTH: 107 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 2:

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Asp Thr Trp
            20                  25                  30

Leu Ala Trp Tyr Gln Gln Lys Pro Gly Lys Ser Pro Gln Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65              70                  75                      80

Glu Asp Phe Val Asn Tyr Tyr Cys Gln Gln Val Tyr Ser Ser Pro Phe
                85                  90                  95

Thr Phe Gly Ala Gly Thr Lys Leu Glu Leu Lys
            100                 105

(2) INFORMATION FOR SEQ ID NO: 3:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 3:

```
GAGATCCAGC TGCAGCAGTC TGGACCTGAG CTGGTGAAGC CTGGGGCTTC AGTGCAGGTA    60

TCCTGCAAGA CTTCTGGTTA CTCATTCACT GACTACAACG TGTACTGGGT GAGGCAGAGC   120

CATGGAAAGA GCCTTGAGTG GATTGGATAT ATTGATCCTT ACAATGGTAT TACTATCTAC   180

GACCAGAACT TCAAGGGCAA GGCCACATTG ACTGTTGACA AGTCTTCCAC CACAGCCTTC   240

ATGCATCTCA ACAGCCTGAC ATCTGACGAC TCTGCAGTTT ATTTCTGTGC AAGAGATGTG   300

ACTACGGCCC TTGACTTCTG GGGCCAAGGC ACCACTCTCA CAGTCTCCTC A            351
```

(2) INFORMATION FOR SEQ ID NO: 4:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 4:

Glu Ile Gln Leu Gln Gln Ser Gly Pro Glu Leu Val Lys Pro Gly Ala
1               5                   10                  15

Ser Val Gln Val Ser Cys Lys Thr Xaa Gly Tyr Ser Phe Thr Asp Tyr
            20                  25                  30

Asn Val Tyr Trp Val Arg Gln Ser His Gly Lys Ser Leu Glu Trp Ile
        35                  40                  45

Gly Tyr Ile Asp Pro Tyr Asn Gly Ile Thr Ile Tyr Asp Gln Asn Phe
    50                  55                  60

Lys Gly Lys Ala Thr Leu Thr Val Asp Lys Ser Ser Thr Thr Ala Phe
65                  70                  75                  80

Met His Leu Asn Ser Leu Thr Ser Asp Asp Ser Ala Val Tyr Phe Cys
                85                  90                  95

Ala Arg Asp Val Thr Thr Ala Leu Asp Phe Trp Gly Gln Gly Thr Thr
            100                 105                 110

Leu Thr Val Ser Ser
        115

(2) INFORMATION FOR SEQ ID NO: 5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 5:

Leu Ala Ser Gln Thr Ile Asp
1               5

(2) INFORMATION FOR SEQ ID NO: 6:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 6:

Ala Ala Thr Asn Leu Ala Asp
1               5

(2) INFORMATION FOR SEQ ID NO: 7:

(i) SEQUENCE CHARACTERISTICS:

(A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 7:

Gln Gln Val Tyr Ser Ser Pro Phe Thr
1               5

(2) INFORMATION FOR SEQ ID NO: 8:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 8:

Thr Asp Tyr Asn Val Tyr
1               5

(2) INFORMATION FOR SEQ ID NO: 9:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 9:

Tyr Ile Asp Pro Tyr Asn Gly Ile Thr Ile Tyr Asp Gln Asn Phe Lys
1               5                   10                  15
Gly (2) INFORMATION FOR SEQ ID NO: 10:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 10:

Asp Val Thr Thr Ala Leu Asp Phe
 1               5

(2) INFORMATION FOR SEQ ID NO: 11:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 11:

CTGGCAAGTC AGACCATTGA T                                              21

(2) INFORMATION FOR SEQ ID NO: 12:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 12:

GCTGCCACCA ACTTGGCAGA T                                              21

(2) INFORMATION FOR SEQ ID NO: 13:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 13:

CAACAAGTTT ACAGTTCTCC ATTCACGT                                             28

(2) INFORMATION FOR SEQ ID NO: 14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 14:

ACTGACTACA ACGTGTAC                                                        18

(2) INFORMATION FOR SEQ ID NO: 15:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 15:

TATATTGATC CTTACAATGG TATTACTATC TACGACCAGA ACTTCAAGGG C                   51

(2) INFORMATION FOR SEQ ID NO: 16:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 16:

GATGTGACTA CGGCCCTTGA CTTC                                                 24

(2) INFORMATION FOR SEQ ID NO: 17:

(i) SEQUENCE CHARACTERISTICS:
            (A) LENGTH: 23 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 17:

GCACCTCCAG ATGTTAACTG CTC                                                        23

(2) INFORMATION FOR SEQ ID NO: 18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 18:

GAARTAVCCC TTGACCAGGC                                                            20

(2) INFORMATION FOR SEQ ID NO: 19:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 19:

GGAGGCGGCG GTTCTGACAT TGTGMTGWCM CARTC                                           35

(2) INFORMATION FOR SEQ ID NO: 20:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 20:

ATTTCAGGCC CAGCCGGCCA TGGCCGARGT YCARCTKCAR CARYC          45

(2) INFORMATION FOR SEQ ID NO: 21:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 21:

CCCGGGCCAC CATGKCCCCW RCTCAGYTYC TKG          33

(2) INFORMATION FOR SEQ ID NO: 22:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 22:

CCCGGGCCAC CATGGRATGS AGCTGKGTMA TSCTC          35

(2) INFORMATION FOR SEQ ID NO: 23:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 23:

ATATACTCGC GACAGCTACA GGTGTCCACT CCGAGATCCA GCTGCAGCAG TC          52

(2) INFORMATION FOR SEQ ID NO: 24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 24:

GACCTGAATT CTAAGGAGAC TGTGAGAGTG G                                31

(2) INFORMATION FOR SEQ ID NO: 25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 25:

TTAATTGATA TCCAGATGAC CCAGTCTCC                                  29

(2) INFORMATION FOR SEQ ID NO: 26:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 26:

TAATCGTTCG AAAAGTGTAC TTACGTTTCA GCTCCAGCTT GGTCC                45